United States Patent [19]

Ashida et al.

[11] 4,066,628

[45] Jan. 3, 1978

[54] OXAZOLIDONE CATALYST

[75] Inventors: Kaneyoshi Ashida, Hiratsuka, Japan; Kurt C. Frisch, Grosse Ille; Panagiotis Kordomenos, Detroit, both of Mich.

[73] Assignee: Mitsubishi Chemical Industries Ltd., Tokyo, Japan

[21] Appl. No.: 710,607

[22] Filed: Aug. 2, 1976

[51] Int. Cl.$^2$ ............................................. C08G 59/14
[52] U.S. Cl. ........................ 260/77.5 R; 260/47 EP; 260/77.5 AB
[58] Field of Search .................. 260/77.5 R, 77.5 AB, 260/47 EP, 18 TN

[56] References Cited

U.S. PATENT DOCUMENTS

| 3,793,236 | 2/1974 | Ashida et al. | 260/77.5 R |
| 3,817,938 | 6/1974 | Ashida et al. | 260/77.5 R |
| 3,960,813 | 6/1976 | Russell et al. | 260/77.5 R |

Primary Examiner—Eugene C. Rzucidlo
Attorney, Agent, or Firm—Gordon W. Hueschen

[57] ABSTRACT

Oxazolidones are produced by reacting an organic isocyanate with an epoxide in the presence of a catalyst selected from the group consisting of dialkyl zinc, zinc carboxylate, organozinc chelate compound and trialkyl aluminum. Polyoxazolidones produced according to the present invention are useful starting materials for the manufacture of a wide variety of product including foams, coatings, adhesives, elastomers and the like.

7 Claims, No Drawings

OXAZOLIDONE CATALYST

BACKGROUND OF THE INVENTION

The preparation of oxazolidones from an organic isocyanate and an epoxide using a quarternary ammonium halide and an alcohol as cocatalysts is disclosed in U.S. Pat. No. 3,313,747. It is also known that zinc bromide catalyzes the foregoing reaction, Sandler, J. Polymer Science A-1, 5, 1481 (1967). Lithium chloride has been found by K. Gulbins to be a catalyst for the reaction between an aromatic isocyanate and an aromatic epoxide. (Chem. Ber. 93, 1875, 1960). n-Butoxy lithium has been found by R. R. Dileone to be an oxazolidone catalyst (J. Polymer Science, Part A-1, Vol. 8, p.609, 1970). An adduct of lithium bromide and tributyl phosphine oxide has been reported by J. E. Herweh and W. J. Kauffman to be an oxazolidone catalyst (Tetrahedron Letters, No.12, p,809, 1971). U.S. Pat. No. 3,702,839 (Nov. 14, 1972) disclosed that a phosphonium salt was an oxazolidone catalyst. S. Kimura and H. Samejima (Japanese Patent Public Disclosure 48-70797, Sept.,25, 1973) disclosed that monomer-soluble catalyst selected from the group consisting of specific organic metal chelates alkyl glycidyl ammonium salts, trialkyl (triaryl or tricycloalkyl)borates, and trialkyl (or triaryl)phosphines are oxazolidone catalysts. Y. Iseda, F. Odaka et al. (Japanese Patent Public Disclosure 49-37999, Apr., 9, 1974) have disclosed that epoxy-soluble quaternary ammonium compounds and/or lithium halide-phosphine oxide complexes are oxazolidone catalysts. U.S. Pat. No. 3,817,938 (June 18, 1974) disclosed that alkoxide or phenoxide of a metals of Group IIA or IIIA of the Periodic Table was an oxazolidone catalyst. It has now been found that the hereinbelow disclosed and claimed dialkyl zinc, zinc carboxylate, organozinc chelate compound and trialkyl aluminum are much more effective catalysts for the preparation of oxazolidones.

SUMMARY OF THE INVENTION

Accordingly, it is an object of this invention to provide novel catalysts for the preparation of oxazolidones.

It is a further object of this invention to provide catalysts which will enable oxazolidones to be prepared efficiently and in relatively high yields.

Still other objects will readily present themselves to one skilled in the art upon reference to the ensuing specification and claims.

DETAILED DESCRIPTION OF THE INVENTION

This invention provides an improved process for preparing oxazolidone and polyoxazolidone products comprising reacting an organic isocyanate with an epoxide in the presence of catalytically effective amount of a catalyst compound selected from the group consisting of $ZnR_2$, $Zn(OCOR)_2$, ZnX and $AlR_3$ wherein R is an alkyl group having 1 to 12 carbon atoms and X is an organic bidentate group.

In preparing polyoxazolidones by the reaction of an organic polyisocyanate with a polyepoxide, the relative amounts of the organic polyisocyanate and the polyepoxide are not critical and the produced polyoxazolidones may be isocyanate-terminated or epoxy-terminated.

The produced polyoxazolidones are useful as starting materials for the manufacture of a wide variety of products. For example, isocyanate-terminated polyoxazolidones can be trimerized to produce isocyanurate foams, coatings, adhesives, elastomers, and the like. In addition, isocyanate-terminated polyoxazolidones can be further polymerized using an amine having at least two reactive amino hydrogen atoms, a polycarboxylic acid, a carboxylic acid anhydride, a polyol, or mixtures of the foregoing. On the other hand epoxy-terminated oxazolidones can be cured in the presence of conventional epoxy-curing agents, e.g., amines or acid anhydride.

The isocyanate-epoxide reaction, catalyzed by the catalyst of the present invention, is usually carried out at an elevated temperature, preferably in the range of about 100° C. to about 170° C. for a time period of from about 2 to about ten hours. The catalyst is present in an amount sufficient to effect the formation of the oxazolidone ring. The exact amount of catalyst present in any particular instance can vary depending on the process conditions but preferably is in the range of about 0.001 weight percent to about 5 weight percent, based on the weight of the reactants. More preferably, the amount of catalyst present is in the range from about 0.01 weight percent to about 2 weight percent.

The term "organic isocyanate" as used herein and in the appended claims is taken to mean an organic compound containing one or more isocyanato (-NCO) groups. Examples of organic monoisocyanates are butyl isocyanate and phenyl isocyanate.

Suitable organic polyisocyanates are those which are commonly used in the preparation of polyurethanes. Illustrative of such polyisocyanates are the tolylene diisocyanates (TDI) such as 2,4-tolylene diisocyanate, 2,6-tolylene diisocyanate, the methylene bis(phenyl isocyanates) (MDI) such as 4,4'-methylene bis(phenyl isocyanate), also dianisidine diisocyanate, toluidine diisocyanate, m-xylylene diisocyanate, 1,5-naphthylene diisocyanate, p-phenylene diisocyanate 1,4-diethylbenzene-$\beta,\beta'$-diisocyanate, hexamethylene diisocyanate, isophorone diisocyanate, 4,4'-methylene bis(cyclohexylisocyanate) and other di- and higher polyisocyanates. Mixtures of two or more of the above isocyanates can also be used, such as mixtures of the 2,4- and 2,6-isomers of tolylene diisocyanate, mixtures of the 2,4'- and 4,4'-isomer of methylene bis(phenyl isocyanate) and the like. In addition to the 4,4'-methylene bis(phenyl isocyanate) or mixtures of the 2,4'-isomer and the 4,4'-isomer thereof which are employed as the isocyanate component, there can also be used modified forms of these isocyanates. For example, there can be used 4,4'-methylene bis(phenyl isocyanate), or an admixture thereof with a minor amount of the 2,4'-isomer, which has been treated to convert a minor proportion generally less than 15% by weight of the starting material, to an artifact of said starting material. For example, the polyisocyanate component can be methylene bis(phenyl isocyanate) which has been converted to a stable liquid at temperatures of about 10° C. and higher.

Illustrative of another modified form of 4,4'-methylene bis(phenyl isocyanate) which can form the polyisocyanate component is the product obtained by heating the former compound, or mixtures thereof with small portions of 2,4'-isomer, with a minor portion of a carbodiimide formation catalyst such as trihydrocarbyl phosphate. In addition to the various modified forms of metnylene bis(phenyl isocyanate) exemplified above there can also be employed as the polyisocyanate component, a mixture of methylene bis(phenyl isocyanate) with methylene-bridged polyphenyl polyisocyanates of higher functionality. Such mixtures are generally those obtained by phosgenation of corresponding mixtures of methylene-bridged polyphenyl polyamines. The latter, in turn, are obtained by interaction of formaldehyde, hydrochloric acid and primary aromatic amines, for example, aniline, o-chloroaniline, o-toluidine and the like. Particularly suitable and thus preferred are organic polyisocyanates obtained by the phosgenation of the reaction products of aniline and formaldehyde, represented by the formula:

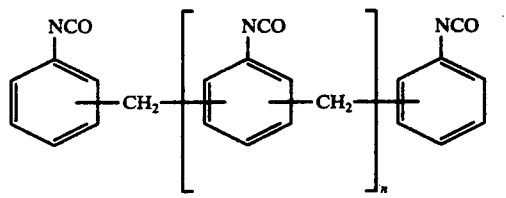

wherein n is an integer having a value in the range from zero to about 10, inclusive.

The term "epoxide" as used herein and in the appended claims is taken to mean a compound containing one or more epoxide.

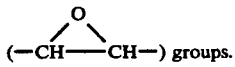

Examples of monoepoxides are phenyl glycidyl ether and epichlorohydrin.

The polyepoxides may contain aromatic, aliphatic, or cycloaliphatic groups together with two or more epoxide

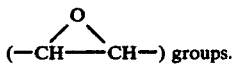

Preferably the polyepoxide is aromatic-based, for example, it contains aromatic groups. Illustrative polyepoxides are:

1. the glycidyl ethers of polyhydric mononuclear and fused ring phenols such as resorcinol, hydroquinone, pyrocatechol, saligenin, phloroglucinol, 1,5-dihydroxynaphthalene, 1,6-dihydroxynaphthalene, 1,7-dihydroxynaphthalene and the like;

2. the glycidyl ethers of non-fused polynuclear phenols represented by the general formula:

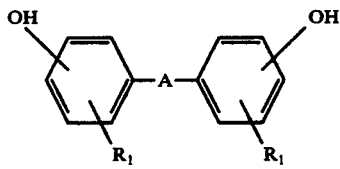

wherein $R_1$ represents 0 to 4 substituents selected from the class consisting of a halogen and lower-alkyl, A is a bridging group selected from the class consisting of

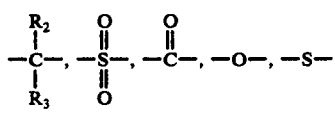

and a single covalent bond, wherein $R_2$ and $R_3$ each represent a moiety selected from the class consisting of hydrogen, lower-alkyl, lower-cycloalkyl and aryl. Typical of such compounds are the diglycidyl ethers of:

4,4'-dihydroxydiphenylsulfone,
4,4'-dihydroxybiphenyl,
4,4'-dihydroxybenzophenone,
bis(4-hydroxyphenyl)methane (bisphenol F),
2,2-bis(4-hydroxyphenyl)butane (bisphenol B),
2,2-bis(4-hydroxyphenyl)propane (bisphenol A),
1,1-bis(4-hydroxyphenyl)propane,
3,3-bis(4-hydroxyphenyl)pentane,
2-(3-hydroxyphenyl)-2-(4-hydroxyphenyl)butane,
1-phenyl-1-(2-hydroxyphenyl)-1-(3-hydroxyphenyl)-propane,
1-phenyl-1, 1-bis(4-hydroxyphenyl)butane,
1-phenyl-1, 1-bis(4-hydroxyphenyl)pentane,
1-tolyl-1, 1-bis(4-hydroxyphenyl)ethane,
bis(3-bromo-4-hydroxyphenyl)methane,
2,2-bis(3-bromo-4-hydroxyphenyl)propane,
bis(3-bromo-4-hydroxyphenyl)diphenylmethane,
1,1-bis(3-bromo-4-hydroxyphenyl)-1-(2,5-dibromophenyl)-ethane,
bis(3,5-dibromo-4-hydroxyphenyl)methane,
2,2-bis(3,5-dibromo-4-hydroxyphenyl)propane,
bis(3,5-dibromo-4-hydroxyphenyl)diphenylmethane,
1,1-bis(3,5-dibromo-4-hydroxyphenyl)-1-(2,5-dibromophenyl)-ethane
bis(3-bromo-4-hydroxyphenyl)sulfone,
bis(3,5-dibromo-4-hydroxyphenyl)sulfone;

3. the glycidyl ethers of novolac resins. The novolac resins are the products obtained by acid condensation of phenol, or a substituted phenol, with formaldehyde and are conventionally represented by the general formula:

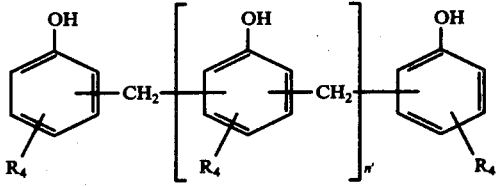

wherein n' has an average value of from about 1 to 12 and $R_4$ represents from 0 to 4 substituents selected from halogen and lower alkyl groups. It is to be understood that the above formula is highly idealized and is an approximation only. A wide range of novolac resins of differing molecular weights is available commercially, all of which are represented approximately by the above formula. Since the class of novolac resins is so well recognized in the art, the epoxides derived therefrom by conversion of the novolacs to their glycidyl ethers (by conventional procedures, for example, reaction with epichlorohydrin) will be referred to hereafter as "novolac resin glycidyl ethers";

4. dicyclopentadiene dioxide, for example, the compound having the formula:

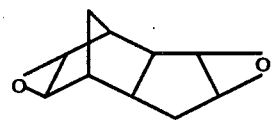

5. vinyl cyclohexane dioxide, for example, the compound having the formula:

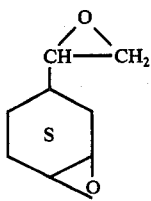

6. The dicyclohexyl oxide carboxylates represented by the general formula:

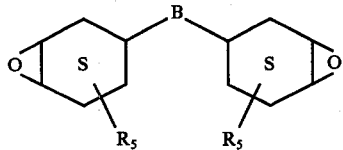

wherein $R_5$ in each instance represents from 0 to 9 lower-alkyl groups, and B represents a divalent radical selected from the class consisting of:

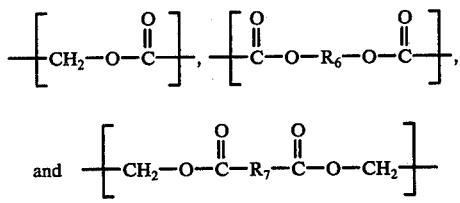

wherein $R_6$ is selected from the class consisting of lower-alkylene and lower-oxyalkylene and $R_7$ is selected from the class consisting of lower-alkylene lower alkenylene and arylene. Examples of the dicyclohexyl oxide carboxylates are:

3,4-epoxycyclohexylmethyl 3,4-epoxycyclohexanecarboxylate,
3,4-epoxy-6-methylcyclohexylmethyl 3,4-epoxy-6-methylcyclohexanecarboxylate
bis(3,4-epoxycyclohexylmethyl)maleate,
bis(3,4-epoxycyclohexylmethyl)succinate,
ethylene bis(3,4-epoxy-6-methylcyclohexanecarboxylate), and the like.

7. The glycidyl derivative of aromatic primary amines represented by the formula:

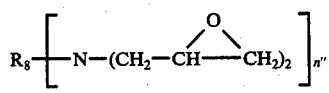

wherein $n''$ is an integer of from 1 to 3 and $R_8$ is an aromatic residue of valency $n''$ selected from the class consisting of aromatic residues having the formulae:

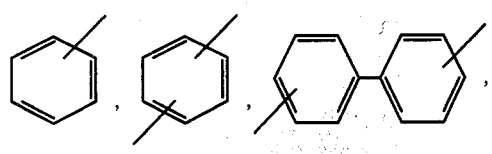

-continued

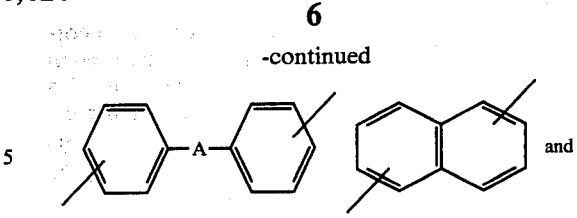

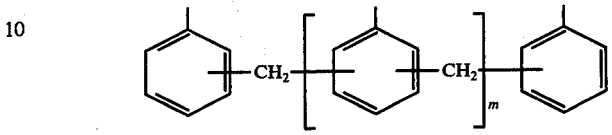

wherein A is a bridging group a hereinbefore defined and $m$ is a number having an average value of from about 0.1 to about 1.0. Illustrative of such compounds are the N,N-diglycidyl derivatives of:

aniline,
2,4-tolylene diamine,
2,6-tolylene diamine,
m-phenylene diamine,
p-phenylene diamine,
4,4'-diamino-diphenyl,
4,4'-diamino-diphenylmethane
2,2-bis(4-aminophenyl)propane,
2,2-bis(4-aminophenyl)butane,
4,4'-diamino-diphenyl sulfide,
4,4'-diamino-diphenyl sulfone,
4,4'-diamino-diphenyl ether,
1,5-diamino-naphthalene, and
methylene-bridged polyphenyl polyamines from about 35 percent by weight to about 85 percent by weight of methylenedianilines, the remaining parts of said mixture being triamines and polyamines of higher molecular weight, said polyamine mixture having been formed by said condensation of aniline and formaldehyde. The latter polyamine mixtures can be prepared by procedures well-known in the art.

The catalyst to be used in the present invention are dialkyl zinc, zinc carboxylate, organozinc chelate compound and trialkyl aluminum. Some examples of dialkyl zinc are diethyl zinc, di-n-propyl zinc, di-n-butyl zinc, ethyl-n-propyl zinc, ethyl-i-butyl zinc, n-propyl-i-butyl zinc and i-butyl-i-amyl zinc, and some examples of trialkyl aluminum are trimethyl aluminum, triethyl aluminum, tri-i-propyl aluminum and tri-n-butyl aluminum. Also suitable are zinc carboxylate, for example, zinc acetate, zinc propionate, zinc butyrate and zinc octoate and organozinc chelate compound such as zinc acetylacetonate.

In addition, suitable are complexes of the said metal alkyls with a compound selected from the group consisting of ethers, tertiary phosphines and tertiary amines. Some examples of the complexes are $(CH_3)_3Al.N(CH_3)_3$, $(CH_3)_3Al.P(CH_3)_3$, $(CH_3)_3Al.O(CH_3)_2$, $(CH_3)_3Al.O(C_2H_5)_2$, $(C_2H_5)_3Al.O(C_2H_5)_2$.

Among the above mentioned compounds, the most preferable catalyst is diethyl zinc.

The relative amount of the polyisocyanate and polyepoxide is not critical. When the equivalent ratio of isocyanate to epoxide (NCO/Epx) is greater than 1, isocyanate-terminated polyoxazolidones are produced, on the contrary, in case of NCO/Epx equivalent ratio being less than 1, epoxy-terminated polyoxazolidones are produced.

Polymerizable polyoxazolidones prepared in accordance with the present invention can be polymerized in the presence of a catalytically effective amount of a polymerization or curing agent which, depending on the polymerization conditions polyoxazolidone with an isocyanate reactive compound such as a polyfunctional amine having at least two reactive amino hydrogen atoms, a polycarboxylic acid, a polycarboxylic anhydride or a polyol having at least two hydroxyl groups.

Typical suitable polyfunctional amines are 2-aminophenol, cyclohexylamine, phenethylamine, aniline, 2-ethylhexylamine, ethylenediamine, butylenediamine, xylylenediamine, hexamethylenediamine, dihexylenetriamine, triethylenetetramine, dipropylenetriamine, p-phenylenediamine, 4,4'-methylenedianiline, and the like.

Typical polycarboxylic acids are aliphatic, cycloaliphatic, and aromatic carboxylic acids such as oxalic acid, malonic acid, maleic acid, glutaric acid, citraconic acid, 1,2-cyclohexanedicarboxylic acid, phthalic acid, 1,8-naphthalenedicarboxylic acid, 3-carboxycinnamic acid, 1,2,4-butanetricarboxylic acid, 1,2,4-hexanetricarboxylic acid, 1,2,4-benzenetricarboxylic acid, and the like.

Suitable polycarboxylic anhydrides are aromatic carboxylic anhydrides, e.g., pyromellitic dianhydride.

Suitable polyols are aliphatic and cycloaliphatic polyalcohols and polyhydric phenols such as ethylene glycol, diethylene glycol, glycerol, polypropylene glycols, butanediol, triethanolamine, pentaerythritol, bis(4-hydroxyphenyl)methane, sorbitol, resorcinol, trimethylolphenol, pyrogallol, hydroquinone, 1,8-naphthalenediol, cyclohexanediol, and the like.

Any suitable blowing agent may be employed for such formulations, if desired, such as inorganic blowing agents, for example, water or boric acid, low-boiling hydrocarbons, for example, pentane, hexane, heptane, pentene, heptene, benzene, etc., halogenated hydrocarbons such as dichlorodifluoromethane, trichlorotrifluorethane, trichlorofluoromethane, and the like. Also suitable are reactive organic blowing agents such as the nitroalkanes, for example, nitromethane, nitroethane, nitropropane, etc., the aldoximes, for example, acetaldoxime, propionaldoxime, etc., acid amides, for example, formamide, acetamide, benzamide, etc., enolizable carbonyl compounds, for example, acetylacetone, acetacetic acid ester, etc., and nitrourea.

Optionally, a surfactant such as a silicone surfactant or a non-ionic surfactant may also be employed if such formulations are foamed. The use of a surfactant is not always necessary, but it is preferable in instances where a relatively fine cell structure is desired. Typical examples of suitable surfactants are siloxane-oxyalkylene block copolymers, vinylsilane-oxyalkylene graft copolymers and the like.

Other optional additives, such as flame retardants and organic or inorganic fillers usually employed in the preparation of polymer foams can also be employed with such formulations. Some of the flame retardants also tend to decrease the viscosity of the formulation during compounding. Illustrative flame retardants are tris (haloalkyl)phosphates such as tris(2-chloroethyl)-phosphate, tris(2-bromoethyl)phosphate, tris(2,3-dichloroethyl) phosphate, tris(2,3-dibromoethyl)phosphate, monoammonium phosphate, ammonium polyphosphates, sodium borate, bis (2-haloalkyl)-2-haloalkanephosphonates such as bis(2-chloroethyl) 2-chloroethane phosphonate, bis(2-chloropropyl) 2-chloropropane phosphonate, bis(2-bromopropyl) 2-bromopropane phosphonate, antimony oxides, polyvinyl chloride resins, dialkyl alkanephosphonates such as dimethyl methylphosphonate, dialkyl allylphosphonate, dimethyl benzylphosphonate, diamyl amylphosphonate, trimethyl phosphorothionate, ethylene phenyl phosphorothionate, tetrahalobisphenols such as tetrachlorobisphenol A, tetrabromobisphenol A, and the like. Said flame retardants are employed in the formulation in the appropriate amounts necessary to impart the desired degree of flame retardancy to the resulting cellular polymer.

Suitable illustrative inert inorganic fillers are calcium carbonate, ammonium phosphate, calcium phosphate, ammonium sulfate, silica, asbestos, glass, mica, carbon black, wood flour, antimony oxides, etc. Illustrative organic fillers are the various polymers, copolymers, and terpolymers of vinyl chloride, vinyl acetate, acrylonitrile, acrylamide, styrene, ethylene, propylene, butadiene, divinyl benzene, and the like. Cellulose and starch can also be employed, if desired.

The use of halogen-containing fillers is particularly advantageous since the use of such materials imparts additional flame resistance to the produced resins whether foamed or cast.

The present invention is further illustrated by the following examples, in which, first of all, the formation of oxazolidone linkage by the reaction of a monoisocyanate with a mono-epoxide was confirmed by determining melting points, elemental analyses, infrared and NMR spectra and followed by the illustration of polyoxazolidone preparation.

The formation of the polyoxazolidone was confirmed by both infrared spectra and rates of conversion of the NCO and the epoxide group. The raw materials used in the present invention were listed in Table I. All the reactions were carried out with dry nitrogen sparging. The solvents were freshly distilled over calcium hydride. Elemental analyses were performed by Midwest Microlab., Ltd., Indianapolis. The infrared absorption spectra were obtained on a Perkin-Elmer Model 457 spectrophotometer using a KBr cell. The NMR spectra were determined on a Varian A-60 spectrometer using TMS as the internal standard. The analytical method employed for direct titration of α-epoxy compounds was the method developed by R. Diskstra and A. M. F. Danhmen, (Analytical Chemical Acta, Vol. 31, p. 38, 1964).

Table I

| Designation | Chemical Identification | Supplier |
|---|---|---|
| Phenyl isocyanate | | Aldrich Chem. Co. |
| Cyclohexyl isocyanate | | Aldrich Chem. Co. |
| Hylene W | 4,4'-methylene bis (cyclohexyl isocyanate) | du Pont |
| TDI | tolylene diisocyanate (80/20) mixture of 2,4- & 2,6-isomers | Allied Chem. Co. |
| H$_{12}$MDI | 4,4'-methylene bis (cyclohexyl isocyanate) | Allied Chem. Co. |
| MDI | 4,4'-methylene bis | The Upjohn Co. |

Table I-continued

| Designation | Chemical Identification | Supplier |
|---|---|---|
| | (phenyl isocyanate) | |
| Phenyl glycidal ether | | Scientific Products |
| Bakelite Epoxy resin ERL-4206 | vinylcyclohexene dioxide | Union Carbide Corp. |
| CIBA Epoxy 6004 | diglycidyl ether of bisphenol A | CIBA-Geigy |
| Epon 828 | diglycidyl ether of bisphenol A | Shell Chem. Co. |
| Diethyl zinc | | Texas Alkyls |
| Di-n-butyl Zinc | | Texas Alkyls |
| Tri-n-butyl aluminum | | Texas Alkyls |
| Toluene | | Sargent-Welch |
| Cellosolve acetate | 2-ethoxyethyl acetate | Union Carbide Corp. |
| Pluracol 710 | polyoxypropylene glycol OH #142 | BASF Wyandotte |
| T-12 | dibutyltin dilaurate | M & T Chem. |
| PMDA | pyromellitic dianhydride | du Pont |
| Aluminum isopropoxide | | Chatten Chemicals |
| DMP-30 | tris 2,4,6(dimethylamino methyl) phenol | Rohm & Haas |
| DMF | dimethyl formamide | Sargent Welch |
| BDMA | benzyldimethylamine | Sherwin Williams |
| TM-MXDA | tetra-methyl-m-xylylene diamine | Sherwin Williams |
| Calcium hydride | | J. T. Baker Chem. Co. |
| Zinc octoate | | Mooney Chem. Inc. |

EXAMPLE 1

Preparation of 5-phenoxymethyl-3-phenyl-2-oxazolidone

A mixture of 29.78g (0.25eq.) of phenyl isocyanate, 37–54g (0.25eq.) of phenyl glycidyl ether and 0.134g (0.2%) of diethyl zinc was heated at 150° C in a three-necked flask under $N_2$. After 10 hrs. the reaction was stopped and the crystalline reaction mass was repeatedly recrystallized from benzene and diethyl ether to yield 22 g (58%) of 5-phenoxymethyl-3-phenyl-2-oxazolidone.

The product had a melting point at 134.8°–135° C. NMR and IR spectra of the product were obtained.

The elemental analysis of the product was as follows:
Anal. Calc. for $C_{16}H_{15}O_3N$ : C, 71.63; H, 5.61; N, 5.20.
Found : C, 71.52; H, 5.69; N, 5.21.

EXAMPLE 2

Preparation of 5-phenoxymethyl-3-cyclohexyl-2-oxazolidone

To a 250 ml three-necked flask was added 37.54g (0.25 eq.) of phenyl glycidyl ether, 31.29g (0.25 eq.) of cyclohexyl isocyanate and 0.137g (0.2%) of diethyl zinc. The reaction mixture was heated to 150° C and held at this temperature for 18 hrs. The NCO percentage and the Epoxy percentage were measured periodically. The product purified by recrystallization from benzene and diethyl ether had a melting point of 137°–138° C. Infrared and NMR spectra of the product were obtained. The elemental analysis of the product was as follows.
Anal. Calc. for $C_{16}H_{21}O_3N$ : C, 69.79; H, 7.69; N, 5.09
Found : C, 69.96; H, 7.97; N, 5.98

EXAMPLE 3 a. Preparation of NCO-terminated polyoxazolidone

To a 500 ml resin flask were added 36g (0.5 eq.) of Bakelite Epoxy resin ERL-4206, 196.5g (1.5 eq.) of Hylene W and 0.2% of diethyl zinc (3.47g of 13.4% solution in toluene). The reaction mixture was heated under nitrogen at 150° C and the NCO percentage as well as the Epoxy percentage was determined. The initial NCO% was 27.0% and the initial Epoxy% was 15.5%. After 10 hrs. of reaction the NCO% dropped to 23.5% and the Epoxy% dropped to 11.8%. At this point another 0.2% of catalyst was added. After 18 hrs. of reaction the NCO% dropped to 19.4% (theoretically it should go down to 18%) and the Epoxy% dropped to 9% (theoretically it should go down to 0%).

b. Preparation of urethane-modifyed poloxazolidone

The prepolymer prepared by the above process a) was diluted in cellosolve acetate to make a 50% solution polyoxypropylene glycol (Pluracol 710) was degassed overnight and a 50% solution in toluene was prepared. The two solutions were mixed together. The ratio of NCO/OH was 2/1. 0.02% of T-12 catalyst was added and the reaction mixture was heated to 80° C. After 5 min. of reaction, a crosslinked product was formed.

EXAMPLE 4

NCO-terminated polyoxazolidone was prepared under the same experimental conditions and procedures as a) in Example 3, except using tributyl aluminium as catalyst in place of diethyl zinc, and heating 15 hrs. in place of heating 10 hrs. A product having NCO content of 26.4% was obtained.

EXAMPLES 5 to 13

NCO-terminated oxazolidone prepolymers were prepared as follows:

94g (0.5 eq.) of glycidyl ether of bisphenol A (in Examples 5 to 7, CIBA Epoxy 6004 was used and in Examples 8 to 13, Epon 828 was used) and 87g (1 eq.) of TDI were charged into a 500 ml reaction resin flask and the reaction system was kept under a blanket of $N_2$. Variety of catalysts (shown in Table II) were charged into the reaction flask with a syringe. The resin flask was put into a constant temperature bath, made of silicone oil and equipped with thermoregulators, mechanical stirrers and variacs, which kept the reaction system at constant temperature. Reaction temperatures were varied. The reaction conditions and the results are shown in Table II. In the Table II, conversion means conversion of TDI.

Table II

| Example No. | Catalyst kind | amount (%) | Temperature °C | Time hrs. | NCO Conversion & |
|---|---|---|---|---|---|
| 5 | Zn(C₂H₅)₂ | 0.1 | 145 | 2 | 46.87 |
| 6 | Zn(C₂H₅)₂ | 0.05 | 145 | 4 | 52.39 |
| 7 | Zn(C₂H₅)₂ | 0.05 | 135 | 5 | 49.28 |
| 8 | Zn(C₂H₅)₂ | 0.1 | 145 | 2 | 49.01 |
| 9 | Zn(C₂H₅)₂ | 0.2 | 120 | 1 | 49.48 |
| 10 | Zn(C₂H₅)₂ | 0.1 | 120 | 1.5 | 49.60 |
| 11 | Zn(n-C₄H₉)₂ | 0.1 | 120 | 5 | 38.23 |
| 12 | Zn(n-C₄H₉)₂ | 0.2 | 120 | 3.5 | 35.79 |
| 13 | Al(n-C₄H₉)₃ | 0.1 | 120 | 5 | 28.27 |

EXAMPLE 14

Preparation of NCO-terminated oxazolidone prepolymer 188g (1 eq.) of Epon 828 and 262g (2 eq.) of $H_{12}MDI$ were charged into a 1-liter reaction resin flask and the reaction system was kept under a blanket of $N_2$. A combined flow of $N_2$ and diethyl zinc was fed through a glass pipe into 450g of cellosolve acetate. An amount of catalyst corresponding to 0.4% of the reactants was dissolved in cellosolve acetate. The catalyst solution was added to the reactants in the resin flask. The resin flask was put into a constant temperature bath, made of silicone oil and equipped with thermoregulators, mechanical stirrers and variacs, which kept the reaction system at 150° C. The free NCO percentage was measured periodically. After 9 hrs. a 63% yield of the product was obtained. By increasing the amount of catalyst to 0.8% of reactants, a 65% yield was realized.

EXAMPLE 15 a. Preparation of NCO-terminated oxazolidone prepolymer 188g of Epon 828 were reacted with 393g of $H_{12}MDI$ at 160° C. NCO/Epoxide equivalent ratio was 3/1. 500g of cellosolve acetate and 0.4% diethyl zinc were used. After 8 hrs. of the reaction, the NCO% dropped to 9.1%. By increasing the amount of catalyst to 0.8% and continuing the reaction for another 5 hrs., NCO% dropped to 8.4% (theoretical amount 8.1%). The resulting equivalent weight of the prepolymer was 500. The solution contained 53.74% solids.

B. Preparation of oxazolidone-imide coatings

A 15% solution of PMDA in DMF was prepared. Equivalent amount of PMDA solution and NCO-terminated oxazolidone prepolymer obtained by the above process a) (Epon 828 + $H_{12}MDI$) were mixed. 0.1% of aluminium isopropoxide was added as catalyst. The mixture was kept under vacuum (10mmHg) for 10 minutes to remove the excess of solvent and $CO_2$ that was formed.

Films with a wet thickness of 8 mils were drawn on glass and aluminium plates and were cured in an oven kept at 145° C for different time periods. The final thickness of the film was from 3 to 4 mils.

The films obtained were clear and transparent. They were very solvent-resistant in a variety of solvents, but they were very brittle. Thermal gravimetric analysis (TGA) was carried out on the films. The temperature of 10% decomposition was 365° C and that of 25% decomposition was 424° C.

EXAMPLE 16

To a 250 ml three-necked flask 18 gms. (0.25 eq.) of ERL-4206, 43.5 gms. (0.5 eq.) TDI and 61.5 gms. of toluene were added. The mixture was heated to 160° C and 0.2% of $Zn(C_2H_5)_2$ was added. After 10 min. from the addition of the catalyst a crosslinked product was formed.

EXAMPLE 17

To a 300 ml three-necked flask 18 gms. (0.25 eq.) of ERL-4206, 65.5 gms. (0.5 eq.) of Hylene W and 83.5 gms. of cellosolve acetate were added. The mixture was heated to 150° C and 0.2% of $Zn(C_2H_5)_2$ was added. The NCO and epoxide percentages were determined every hour. After 10 hrs. the reaction was completed. Films were made from this prepolymer using DMP-30 as crosslinking agent. The films were cured for 8 hrs. at 150° C. Their appearance was rather poor but they exhibited good solvent resistance.

EXAMPLE 18 a. Preparation of poly(oxazolidone-epoxides).

To a 300 ml three-necked flask 47 gms. (0.25 eq.) of Epon-828, 16.375 gms. (0.125 eq.) Hylene W and 63.3 gms. of cellosolve acetate were added. The mixture was heated to 150° C and 0.5% $Zn(C_2H_5)_2$ was added (a solution of $Zn(C_2H_5)$ in toluene was used). The NCO and epoxide percentages were measured periodically and after 7 hrs., when the % conversion of the epoxide group reached 50%, the reaction was stopped.

b. Curing of poly(oxazolidones-epoxides) (Hylene W + Epon-828, NCO/Epoxide = 1/2). The epoxide-terminated prepolymer was cured using pyromellitic dianhydride (PMDA) as curing agent and a tertiary amine (DMP-30, at 1% ratio) as accelerator.

The films were cured at 150° C overnight.
The properties of the obtained film were shown in Table III.

EXAMPLE 19

A. Preparation of poly-2-oxazolidone.

To a 300 ml three-necked flask 47 gms. (0.25 eq.) of Epon-828, 32.75 gms. (0.25 eq.) Hylene W and 119.6 gms. of cellosolve acetate (40% solution) were added. The mixture was heated to 150° C and 0.5% $Zn(C_2H_5)_2$ (a solution of $Zn(C_2H_5)_2$ in toluene) was added. The NCO and epoxide percentages were measured periodically and the reaction was stopped when 90% conversion was measured (after 8 hrs.).

b. Curing of poly-2-oxazolidone (Hylene W + Epon-828, NCO/Epoxide = 1/1).

Films with wet thickness of 8 mils were drawn on glass, aluminum and steel plates. The films were cured in an oven and kept at 150° C for different time periods ranging from 5 to 12 hours.

The properties of the obtained film were shown in Table III.

EXAMPLE 20 a. Isocyanate-terminated polyoxazolidone prepolymer.

Epon-828 and Hylene W were reacted at three different equivalent ratios of NCO/Epoxide, namely, 2/1, 2.5/1, 3/1. The procedure that was followed was the same as the one that was followed for the poly-2-oxazolidone (NCO/Epoxide = 1/1).

b. Curing of poly(oxazolidone-isocyanate) (Hylene W + Epon-828, NCO/Epoxide = 2/1, 2.5/1, 3/1).

The NCO-terminated-prepolymers were cured using DMP-30 as a trimerization catalyst. A 20% solution of potassium acetate was prepared. This solution was mixed with DMP-30 at a ratio of 1:4 (1 solution, 4 DMP-30). This catalyst speeded up the curing process even when temperatures lower than 150° C were used. Lower amounts of catalyst were required than when DMP-30 alone was used.

The properties of the films were shown in Table III.

TABLE III

| | PROPERTIES OF POLYOXAZOLIDONES | | | | |
|---|---|---|---|---|---|
| Example No. | 18 | 19 | 20 | 20 | 20 |
| NCO/Epx ratio (equivalent) | 1/2* | 1/1 | 2/1** | 2.5/1** | 3/1** |
| Properties of the film | | | | | |
| Sward Hardness | 60 | 42 | 40 | 38 | 30 |
| Gardner Impact: lb. in. | | | | | |
| Direct | 40 | 90 | 70 | 60 | 60 |
| Reverse | 30 | 70 | 55 | 50 | 50 |
| Solvent Resistance | Excellent | Excellent | Excellent | Excellent | Excellent |
| Tensile Strength, psi | 6548 | 3006 | 6440 | *** | *** |
| Elongation % | 3.0 | 2.0 | 2.25 | *** | *** |
| TGA | | | | | |
| 10% decomposition Temp. (° C) | 300 | 325 | 302 | 315 | 300 |
| 50% decomposition Temp. (° C) | 435 | 435 | 405 | 470 | 390 |

*Cured with PMDA and DMP-30 at 150° C
**Cured with DMP-30 at 150° C
***Too brittle to test

EXAMPLE 21

To a 250 ml three-necked flask was added 15.625 gms. (0.125 eq.) MDI, 47 gms. (0.25 eq.) Epon-828 and 62.62 gms. of cellosolve acetate. The mixture was heated to 150° C and 0.5% $Zn(C_2H_5)_2$ was added. Five minutes after the addition of the catalyst, a crosslinked product was formed. The same reaction was carried out with the addition of the catalyst taking place at room temperature and the mixture was gradually heated to 150° C. After 30 min., a crosslinked product was formed.

EXAMPLE 22 a. Preparation of polyimide prepolymer.

21.8 gms. of PMDA were dissolved in 80 gms. of DMF and 12.5 gms. of MDI were dissolved in 40 gms. of DMF. The MDI solution was added dropwise to the PMDA solution at 80° C. After the addition of the MDI solution was completed, the temperature was raised to 140° C and the reaction was continued for 12 hours.

b. Preparation of poly(oxazolidone-imides).

The above anhydride-terminated polyimide prepolymer was mixed with an equivalent amount of NCO-terminated polyoxazolidone prepolymer made from Hylene W and Epon-828. 50% DMF was used as a solvent and after refluxing overnight, 83% conversion (as measured by NCO determination) was reached. Films of the above polymer were drawn on glass and steel plates.

The poly(oxazolidone-imide) films, although rather brittle, exhibited good impact strength (60 lb. in.) and excellent solvent resistance. The thermal stability was also very good.

EXAMPLE 23

To a 250 ml three-necked flask were added 11.9 gms (0.1 eq) phenyl isocyanate, 15.0 gms (0.1 eq) phenyl glycidyl ether, 0.4 gm zinc acetate $[Zn(OCOCH_3)_2.2H_2O]$ and 73.1 gms cellosolve acetate. After 7 hours of reaction at 150° C the NCO conversion reached to 100%. The reactant was left overnight and a crystalline product was obtained. The yield of the product (5-phenoxymethyl-3-phenyl-2-oxazolidone) was 18.1%.

EXAMPLE 24

To a 250 ml three-necked flask were added 11.912 gms (0.1 eq) phenyl isocyanate, 15.018 gms (0.1 eq) of phenyl glycidyl ether, 0.4% of zinc acetylacetonate and 100 gms of cellosolve acetate. After 12 hours of reaction at 150° C the NCO conversion reached to 100%, the epoxide conversion 66% and the yield in oxazolidone was 65%.

EXAMPLE 25

The reaction of Example 24 was repeated except using 0.4% zinc octoate instead of zinc acetylacetonate. After 12 hours of reaction the NCO conversion was 100%, the epoxide conversion was 79% and the yield of oxazolidone was 72%.

We claim:

1. A process for preparing oxazolidones which comprises reacting an organic isocyanate with an epoxide in the presence of from 0.001 to 5 weight percent, based on the reactants, of a catalyst selected from the group consisting of $ZnR_2$, $Zn(OCOR)_2$, $ZnX$ and $AlR_3$ wherein R is an alkyl group having 1 to 12 carbon atoms and X is an organic bidentate group.

2. A process for preparing polyoxazolidones which comprises reacting an organic polyisocyanate with a polyepoxide in the presence of from 0.001 to 5 weight percent, based on the reactants, of a catalyst selected from the group consisting of $ZnR_2$, $Zn(OCOR)_2$, $ZnX$ and $AlR_3$ wherein R is an alkyl group having 1 to 12 carbon atoms and X is an organic bidentate group.

3. A process according to claim 2 wherein the catalyst is $ZnR_2$ wherein R is an alkyl group having 1 to 12 carbon atoms.

4. A process according to claim 3, wherein the catalyst is diethyl zinc.

5. A process according to claim 2 wherein the catalyst is zinc octoate.

6. A process according to claim 2 wherein the catalyst is zinc acetylacetonate.

7. A process according to claim 2 wherein 4,4'-methylene bis(cyclohexyl isocyanate) is used as the organic polyisocyanate at a ratio of less than one equivalent per equivalent of the polyepoxide.

* * * * *

UNITED STATES PATENT OFFICE
CERTIFICATE OF CORRECTION

Patent No. 4,066,628              Dated  Jan. 3, 1978

Inventor(s)  Ashida Kaneyoshi

It is certified that error appears in the above-identified patent and that said Letters Patent are hereby corrected as shown below:

Col. 11, line 5: "NCO Conversion &" should read
-- NCO Conversion %--

Signed and Sealed this

Thirteenth Day of June 1978

[SEAL]

Attest:

RUTH C. MASON
*Attesting Officer*

DONALD W. BANNER
*Commissioner of Patents and Trademarks*